United States Patent
Lim et al.

(10) Patent No.: US 9,554,758 B2
(45) Date of Patent: Jan. 31, 2017

(54) SENSOR INTEGRATED PROTECTION PAD FOR SHIELDING RADIATION

(71) Applicants: Vatech Co., Ltd., Gyeonggi-do (KR); Vatech Ewoo Holdings Co., Ltd., Gyeonggi-do (KR)

(72) Inventors: Hyung Keun Lim, Gyeonggi-do (KR); Jin Pyo Chun, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 0 days.

(21) Appl. No.: 14/720,234

(22) Filed: May 22, 2015

(65) Prior Publication Data

US 2015/0335298 A1   Nov. 26, 2015

(30) Foreign Application Priority Data

May 22, 2014 (KR) .................. 10-2014-0061638

(51) Int. Cl.
| | |
|---|---|
| *G01J 1/00* | (2006.01) |
| *A61B 6/10* | (2006.01) |
| *G21F 1/08* | (2006.01) |
| *A61B 6/14* | (2006.01) |
| *G21F 3/00* | (2006.01) |

(52) U.S. Cl.
CPC .............. *A61B 6/107* (2013.01); *A61B 6/145* (2013.01); *G21F 1/08* (2013.01); *G21F 3/00* (2013.01)

(58) Field of Classification Search
CPC ....... A61B 6/4423; A61B 8/565; A61B 6/145; A61B 6/107; G21F 1/08; G21F 3/00
USPC ....................................... 250/336.1
See application file for complete search history.

(56) References Cited

U.S. PATENT DOCUMENTS

| | | | | |
|---|---|---|---|---|
| 5,016,292 A | * | 5/1991 | Rademacher | A61F 9/022 128/858 |
| 5,140,710 A | * | 8/1992 | Rademacher | A61F 9/022 2/426 |
| 5,434,418 A | * | 7/1995 | Schick | G01T 1/2018 250/370.09 |
| 6,754,909 B1 | * | 6/2004 | Samelian | A41D 13/11 2/206 |
| 2004/0218140 A1 | * | 11/2004 | Bleau | A61F 9/026 351/92 |
| 2006/0143766 A1 | * | 7/2006 | Ramsey | A61F 9/02 2/15 |
| 2007/0080300 A1 | * | 4/2007 | Mandelkern | G01T 1/2018 250/370.11 |

(Continued)

*Primary Examiner* — David J Makiya
*Assistant Examiner* — Taeho Jo
(74) *Attorney, Agent, or Firm* — IP Legal Services, LLC

(57) ABSTRACT

A sensor integrated protection device is disclosed. This device includes a sensor for detecting radiations; and a radiation shielding pad to which the sensor is coupled. A data communicating device is placed within radiation shielding pad and electrically coupled to the sensor. This device is suitable for easy wear with the pad shape and can be used for protecting different parts of the body with the various type of the pad holders. In the sensor integrated protection device, the data communicating unit is not built in the sensor but is configured to the sensor outside of the sensor to reduce the size of the sensor and to improve the convenience of using and keeping the sensor.

13 Claims, 4 Drawing Sheets

(56) References Cited

U.S. PATENT DOCUMENTS

| | | | |
|---|---|---|---|
| 2007/0080308 A1* | 4/2007 | Mousavi Yeganeh | G21F 3/00 250/515.1 |
| 2008/0025467 A1* | 1/2008 | Diederich | G03B 42/042 378/168 |
| 2008/0032252 A1* | 2/2008 | Hayman | A61B 5/0088 433/29 |
| 2008/0067392 A1* | 3/2008 | Miyaguchi | G01T 1/2018 250/370.11 |
| 2008/0096156 A1* | 4/2008 | Rose | A61C 1/0015 433/29 |
| 2009/0010396 A1* | 1/2009 | Allmer | G03B 42/042 378/169 |
| 2009/0142724 A1* | 6/2009 | Rosenblood | A61B 1/24 433/29 |
| 2010/0098220 A1* | 4/2010 | Allmer | G03C 3/003 378/169 |
| 2010/0166151 A1* | 7/2010 | Schmulenson | G03B 42/042 378/167 |
| 2010/0210161 A1* | 8/2010 | Jensen | D06M 11/53 442/132 |
| 2011/0150185 A1* | 6/2011 | Uzbelger Feldman | A61B 6/14 378/191 |
| 2011/0280378 A1* | 11/2011 | Feltz | A61B 6/145 378/191 |
| 2012/0070798 A1* | 3/2012 | Teitelbaum | A61C 19/004 433/29 |
| 2014/0198901 A1* | 7/2014 | Christoff | A61B 6/145 378/98 |
| 2015/0250436 A1* | 9/2015 | Hyde | G21F 1/085 378/62 |

* cited by examiner

SENSOR INTEGRATED PROTECTION PAD FOR SHIELDING RADIATION

CROSS REFERENCE TO PRIOR APPLICATIONS

The present application claims priority under 35 U.S.C. §119 to Korean Patent Application No. 10-2014-0061638 (filed on May 22, 2014).

BACKGROUND OF THE INVENTION

Field of the Invention

The present invention relates, in general, to a radiation protection pad for shielding radiation, and, more particularly, to a sensor integrated protection pad.

Description of the Related Art

In general, a radiation imaging apparatus like an X-ray imaging equipment captures images of the inside of a subject by detecting radiation transmitted through the subject with a radiation detector or sensor, and it has been used variously for diagnosing patients in a hospital and testing a test material in a laboratory in a non-destructive manner. For an example, at the dentist, an intraoral sensor detecting the radiation is placed within in a mouth and radiation irradiation is performed outside the mouth to obtain image of teeth, the alveolar bone and facial bones.

Since the radiation used for diagnostic purposes exerts an adverse effect on the human body, it is important to prevent the human body from being exposed to the excessive radiation or to unnecessary radiation.

In order to protect the organs or structure of the human body to be imaged and to prevent regions not to be imaged being exposed to the radiation, it is common to use a radiation shielding equipment or radiation protective clothing for patients.

The conventional radiation protective clothing has the problem of heavy weight and being directly contacted to the skin of patients. This direct contact may cause unexpected radiation contamination. Specifically, the conventional radiation protective clothing used in the dentist is helpful to protect thyroid and regions around the thyroid from the radiation but it is not suitable to protect eyes and their surroundings.

Further, the conventional radiation protective clothing is separated from the radiation detector or the sensor. This causes inconvenience of using the radiation protective clothing during the radiography and keeping it after the use.

SUMMARY OF THE INVENTION

The present invention provides a sensor integrated protection device capable of shielding radiations irradiated from a radiation generating device or scattered radiations on a various positions of a patient as well as convenient in using and keeping owing to a integrated configuration with a sensor.

In accordance with an aspect of the present invention, there is provided a sensor integrated protection device including a sensor for detecting radiations; and a radiation shielding pad to which the sensor is coupled.

In accordance with an aspect of the present invention, the sensor integrated protection device may further include a data communicating device configured to be placed within radiation shielding pad and electrically coupled to the sensor.

In accordance with an aspect of the present invention, the sensor is an intra oral sensor.

In accordance with an aspect of the present invention, the radiation shielding pad includes a base pad; and a plurality of radiation shielding layers covering the base pad in part.

In accordance with an aspect of the present invention, the radiation shielding pad is formed with a base pad.

In accordance with an aspect of the present invention, the base pad is made of radiation shielding material including at least one metal selected or combined from lead (Pb), carbon steel, tungsten (W), stainless steel and Titanium (Ti) or barium compound including $BaSO_4$.

In accordance with an aspect of the present invention, the front surface of the radiation shielding layers are coated with a antireflection material.

In accordance with an aspect of the present invention, the sensor integrated protection device of claim 1 may further include a sensor holder.

In accordance with an aspect of the present invention, the sensor holder is configured to hold the sensor between two radiation protection layers.

In accordance with an aspect of the present invention, the sensor integrated protection device may further include a pad holder for holding the radiation shielding pad.

In accordance with an aspect of the present invention, the pad holder is configured to stand on a floor or to fixed on a wall.

In accordance with an aspect of the present invention, the pad holder has a shape of the eyeglass temples connected to a side of the radiation protection pad.

BRIEF DESCRIPTION OF THE DRAWINGS

The above and other features and other advantages of the present invention will be more clearly understood from the following detailed description when taken in conjunction with the accompanying drawings, in which.

DETAILED DESCRIPTION OF THE INVENTION

Hereinbelow, preferred embodiments of the present invention will be described in detail with reference to the accompanying drawings.

Figure 1:
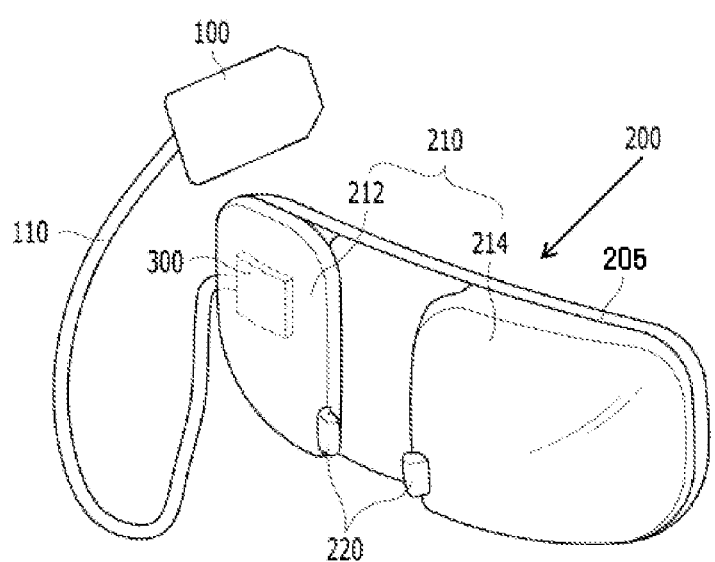
FIG. 1 is a schematic view of a sensor integrated protection device according to an embodiment of the present invention.

Referring to FIG. 1, a sensor integrated protection device according to an embodiment of the present invention may include a sensor 100 and a radiation shielding pad 200. The sensor integrated protection device may further include a data communicating device 300 configured to be placed within radiation shielding pad 200 and electrically coupled to the sensor 100 through wires or without wire.

The sensor 100 detects radiation. Specifically, the sensor 100 may be a digital intra oral sensor which generates electric signals by detecting X-rays irradiated from an X-ray generating device and passed teeth and bones in a mouth.

The sensor 100 may be configured to generate the electric signals in a direct conversion manner or with an indirect conversion manner. The former let radiations be directly converted into electric signal while the latter let the radiations first be converted into visible rays and then the visible rays are converted into the electric signals. In case of adopting the direct conversion manner, a photoelectric conversion device for converting the radiations into the electric signals with a semiconductor material and a signal processing device for generating image signals from the electric signals are required to configure the sensor 100. For the indirect conversion manner, a scintillating layer and a digital image sensor for detecting the visible rays may be used to configure the sensor 100.

The sensor 100 and the data communicating device 300 are coupled through a cable 110 through which the electric signals or the image signals are transmitted. In accordance with embodiments of the present invention, the cable 110 may be integrated to the sensor 100, or the sensor 100 may be configured to have a connector (not shown) so that the cable 110 may be attachable to the connector.

The radiation shielding pad 200 may include a base pad 205 and a plurality of radiation shielding layers 212 and 214 formed on the base pad 205 as shown in FIG. 1. As another example, the radiation shielding layers 212 and 214 may be omitted when the base pad 205 itself is made of radiation shielding material or to contain the radiation shielding material therein. The radiation shielding material may be at least one metal selected or combined from lead (Pb), carbon steel, tungsten (W), stainless steel and Titanium (Ti) or barium compound including $BaSO_4$.

The front surface of the radiation shielding layers 212 and 214 may be coated with a antireflection material to prevent the radiations from being reflected on the front surface of the radiation shielding layers 212 and 214. In case of omitting the radiation shielding layers 212 and 214, whole front surface of the base pad 205 may be coated with the antireflection material to prevent the radiations from being reflected on the surface of the base pad 205. If the radiation shielding layers 212 and 214 are formed, a part of the base pad 205 not covered with the radiation shielding layers 212 and 214 may be coated with the antireflection material.

The data communicating device 300 may be placed within the base pad 205, within the radiation protect layer 212 or 214, between the base pad 205 and the radiation protect layer 212 or 214, at one side of the base pad 205 or at one side of the radiation protect layer 212 or 214. The electric signals or image signals output from the sensor 100 may be transmitted to an external signal processing device (not shown) by the data communicating device 300. The data communicating device 300 may be configured to have a wireless data communication module adopting contactless near field communication (NFC). In the sensor integrated protection device according to the present invention, the data communicating device 300 is equipped and coupled to the sensor 100 for improving convenience of users. Compared with the conventional intra oral sensor, it is possible to remove the data communicating device from the intra oral sensor and to put the data communicating device outside of the intra oral sensor. Thus, it is possible to manufacture the smaller and thinner intra oral sensor. Further, the data communicating device 300 may be configured to have a terminal (not shown) exposed to the outside at one side of the data communicating device 300 so that the cable 110 connected to the sensor 100 may be attachable to and detachable from the data communicating device 300. This brings an advantage in reducing the maintenance cost because the cable 110 can be replaced with new one if there is damage on the cable 110.

The sensor integrated protection device according to the present invention may further include a sensor holder 220. For an example, the sensor holder 220 may be configured to hold the sensor 110 between the two radiation protection layers 212 and 214 as show in FIG. 4. The sensor holder 220 may have a grove where a side edge of the intra oral sensor 110 is inserted. This sensor holder 220 may improve the convenience of keeping the sensor integrated protection pad.

Figure 2:
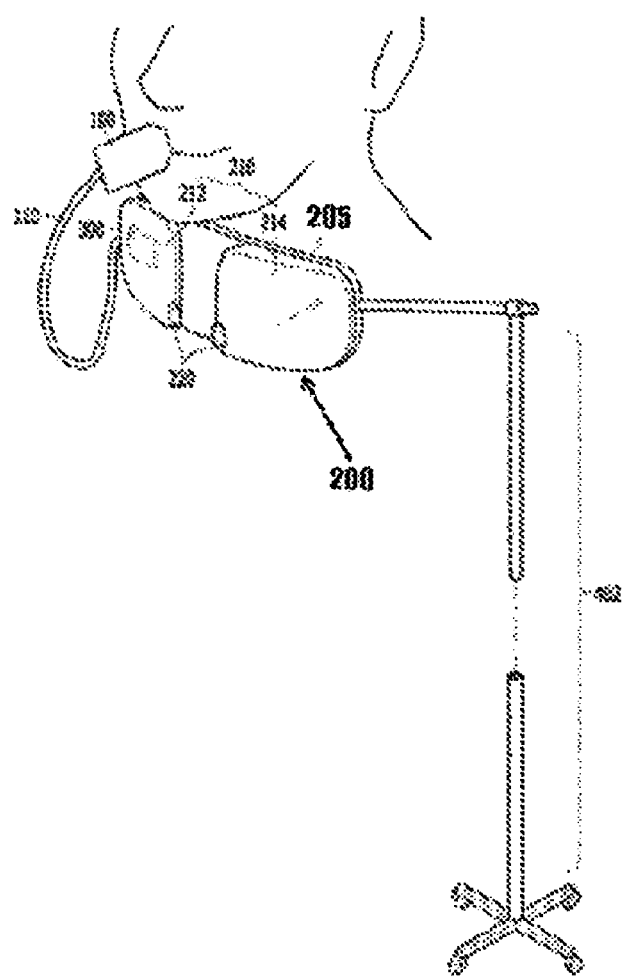
FIG. 2 is an example of using the sensor integrated protection device according to the embodiment of the present invention of FIG. 1.
Figure 3:
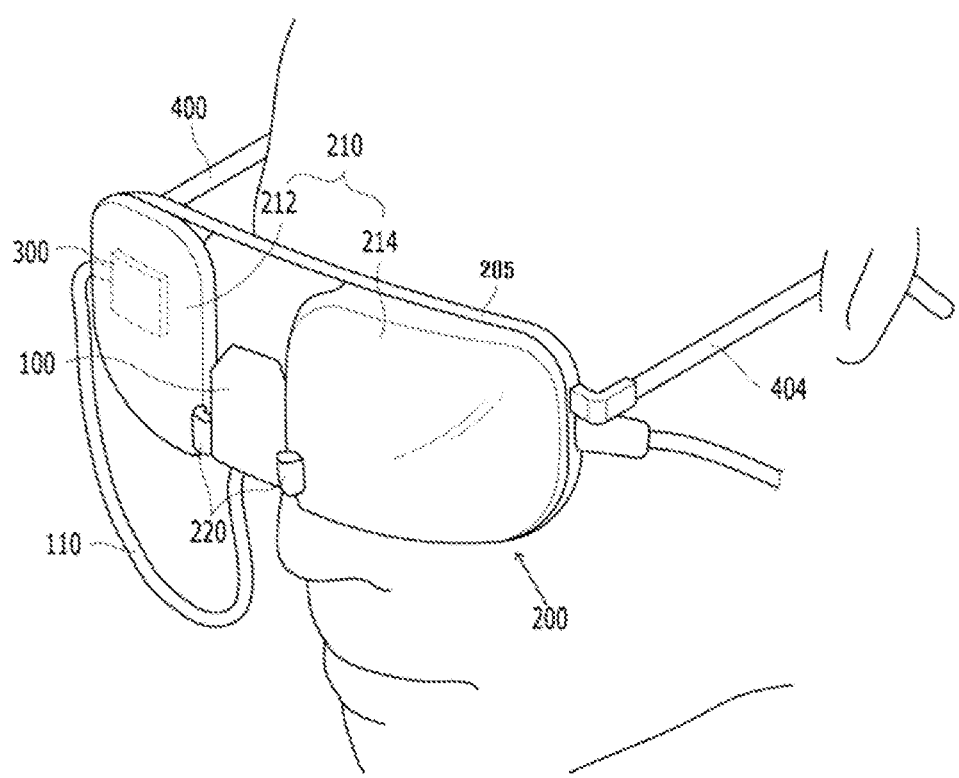
FIG. 3 is another example of using the sensor integrated protection device according to the embodiment of the present invention of FIG. 1.

The sensor integrated protection device according to the present invention may further include a pad holder. A pad holder 402 for holding the radiation shielding pad 200 is configured to stand on a floor as shown in FIG. 2. A part of the rear side or one side of the radiation shielding pad 200 may be connected to be rotatable in a horizontal or vertical direction to the floor. The length of the pad holder 403 may be changeable. The pad holder 402 configured to stand on the floor may be useful to prevent parts of human body such as the eyes or the thyroid from the being exposed to the radiations. The pad holder may be configured to be fixed on a wall. Further, the pad holder may be formed at side edges of the base pad 205. As shown in FIG. 3, in case pad holders 400 and 404 have a shape of the eyeglass temples, the patient can wear the radiation shielding pad 200 like eyeglasses. If the end of the pad holders 400 and 400 are connected, the patient can wear the radiation shielding pad 200 around its neck or on a part of the body like a ring or a band. The lengths of these pad holders 400 and 404 can be changeable.

Figure 4:
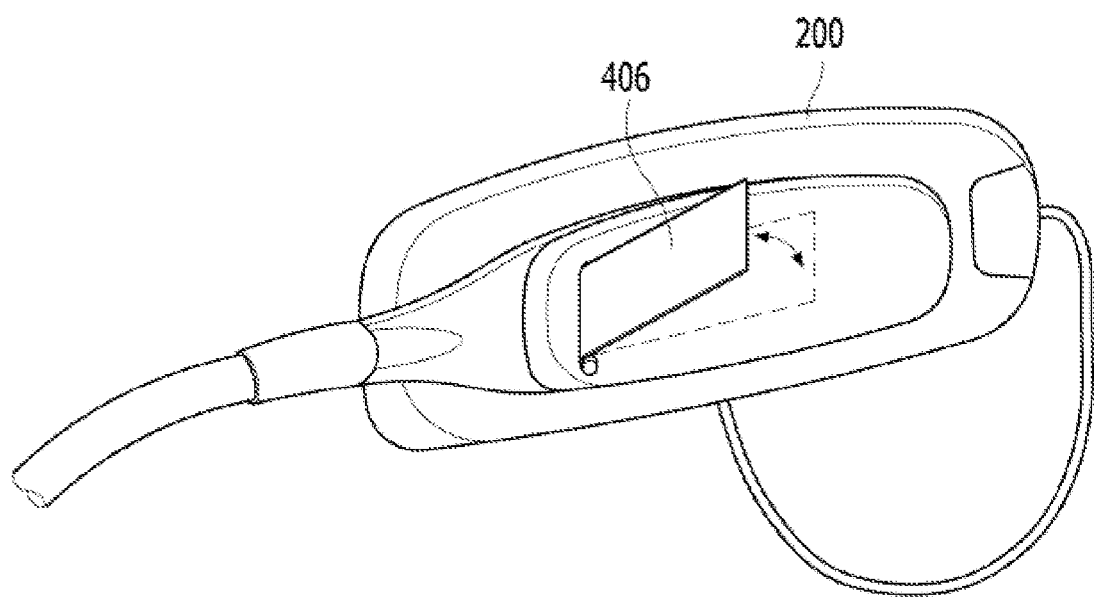
FIG. 4 is a schematic view of a sensor integrated protection device according to another embodiment of the present invention.

Referring to FIG. 4, a pad holder 406 may be formed like a clip for attaching or fixing the radiation shielding pad 200 to where the pad holder 406 to be hanged or fixed.

The sensor integrated protection devices in accordance with the present invention are suitable for easy wear owing to the pad shape and can be used for protecting different parts of the body owing to the various type of the pad holders. In the sensor integrated protection devices according to the present invention, the data communicating unit is not built in the sensor but is configured outside of the sensor. Thus, it is possible to reduce the size of the sensor and to improve the convenience of using and keeping the sensor.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A sensor integrated protection device comprising:
   a sensor for detecting radiations passing through a first part of a target object; and
   a radiation shielding pad physically separated from the sensor in a predetermined distance, configured to protect a second part of the target object from being exposed to the radiations, and configured to include a data communicating device for receiving a sensing result from the sensor and transmitting the sensing result to a predetermined device physically separated from the sensor and the radiation shielding pad,
   wherein the first part of the target object is distanced from the second part of the target object.

2. The sensor integrated protection device of claim 1, wherein the data communication device configure to be placed within radiation shielding pad and electrically coupled to the sensor through a cable.

3. The sensor integrated protection device of claim 1, wherein the sensor is an intra oral sensor.

4. The sensor integrated protection device of claim 1, wherein the radiation shielding pad includes:
   a base pad; and
   a plurality of radiation shielding layers covering the base pad in part.

5. The sensor integrated protection device of claim 1, wherein the radiation shielding pad is formed with a base pad.

6. The sensor integrated protection device of claim 4, wherein the base pad is made of radiation shielding material including at least one metal selected or combined from lead (Pb), carbon steel, tungsten (W), stainless steel and Titanium (Ti) or barium compound including BaSO4.

7. The sensor integrated protection device of claim 4, wherein the front surface of the radiation shielding layers are coated with a antireflection material.

8. The sensor integrated protection device of claim 1, further comprising a sensor holder.

9. The sensor integrated protection device of claim 1, further comprising a sensor holder, and wherein the radiation shielding pad includes a base pad and a plurality of radiation shielding layers covering the base pad in part and the sensor holder may be hold between two radiation protection layers.

10. The sensor integrated protection device of claim 1, further comprising a pad holder for holding the radiation shielding pad.

11. The sensor integrated protection device of claim 10, wherein the pad holder is configured to stand on a floor or to fixed on a wall.

12. The sensor integrated protection device of claim 10, wherein the pad holder has a shape of the eyeglass temples connected to a side of the radiation shielding pad.

13. The sensor integrated protection device of claim 1, wherein the data communication device comprises a wireless data communication module.

* * * * *